United States Patent [19]

Eagar, Jr. et al.

[11] Patent Number: 4,491,676

[45] Date of Patent: Jan. 1, 1985

[54] ACID ADDITION TO AQUEOUS DIALDEHYDE SOLUTIONS

[75] Inventors: Robert G. Eagar, Jr., Yorktown Heights; Gerald J. Murphy, Wappinger Falls, both of N.Y.

[73] Assignee: Union Carbide Corporation, Danbury, Conn.

[21] Appl. No.: 508,468

[22] Filed: Jun. 28, 1983

Related U.S. Application Data

[63] Continuation of Ser. No. 314,347, Oct. 23, 1981, abandoned, which is a continuation of Ser. No. 221,506, Dec. 30, 1980, abandoned.

[51] Int. Cl.$^3$ .............................................. C07C 45/86
[52] U.S. Cl. .................... 568/449; 568/421; 568/594; 568/603
[58] Field of Search ................ 568/449, 421, 603, 594

[56] References Cited

U.S. PATENT DOCUMENTS

| | | | |
|---|---|---|---|
| 2,233,428 | 3/1941 | O'Brien | 424/75 |
| 2,786,081 | 3/1957 | Kress | 424/75 |
| 2,801,216 | 7/1957 | Yoder et al. | 568/494 |
| 3,057,775 | 10/1962 | Rendon | 424/75 |
| 3,897,503 | 7/1977 | Wessendorf et al. | 568/494 |
| 4,244,876 | 1/1981 | Warner et al. | 568/497 |
| 4,302,131 | 3/1982 | Murphy | 568/494 |

FOREIGN PATENT DOCUMENTS

| | | | |
|---|---|---|---|
| 1297489 | 11/1972 | United Kingdom | 424/333 |
| 1405785 | 9/1975 | United Kingdom | 424/333 |
| 2012263 | 7/1979 | United Kingdom | 568/449 |
| 1588648 | 4/1981 | United Kingdom | 424/333 |

OTHER PUBLICATIONS

Dermer et al., J.A.C.S., vol. 77, pp. 1285–1286 (1955).
Boucher, Chem. Abst., vol. 82, #7617h (1974).

*Primary Examiner*—James H. Reamer
*Attorney, Agent, or Firm*—Henry H. Gibson

[57] ABSTRACT

Described herein is a process for rapidly obtaining a stable freeze point depressed aqueous solution comprising a dialdehyde and an aliphatic monohydroxyl alcohol and/or polyhydroxyl alcohol by adding thereto a catalytic amount of a strong acid. Also included herein is a method for liberating the dialdehyde in the aqueous solution by dilution with water and the addition of a catalytic amount of a strong acid.

11 Claims, No Drawings

ACID ADDITION TO AQUEOUS DIALDEHYDE SOLUTIONS

This application is a continuation of prior application Ser. No. 314,347, filed Oct. 23, 1981, now abandoned; which is a continuation of prior application Ser. No. 221,506, filed Dec. 30, 1980 now abandoned.

This invention is directed to a process for rapidly obtaining a stable freeze point depressed aqueous solution comprising a dialdehyde and an aliphatic monohydroxyl alcohol and or polyhydroxy alcohol by adding thereto a catalytic amount of a strong acid. Also, included herein is a method for liberating the dialdehyde in the aqueous solution by dilution with water and the addition of a catalytic amount of a strong acid.

Aqueous solutions of glutaraldehyde are well known commercially available materials useful for killing or inhibiting the growth of microorganisms. These aqueous solutions of glutaraldehyde have been used to control the growth of bacteria in a number of different environments. For example, glutaraldehyde solutions have been used to disinfect medical and surgical supplies and household objects. Further, as described in U.S. Pat. No. 2,801,216 glutaraldehyde solutions have been used to control bacteria in water flooding operations for the secondary recovery of oil and used to prevent corrosion and plugging of iron equipment due to the action of bacteria in storage vessels and associated plumbing and equipment. Thus, it can be seen that there are occasions when glutaraldehyde solutions are stored out of doors and may be subjected to freezing conditions. The freezing points of a 25 percent aqueous solution of glutaraldehyde is about 22° F. Therefore, it would be desirable under these conditions to further depress the freezing point of the aqueous solution of glutaraldehyde. However, any additive to the aqueous glutaraldehyde solution which could depress the freezing point of the solution must not decrease the chemical or biological activity of the solution at time of use and must be one which maintains the freezing point at the desired temperature. That is, the additive should be one which is able to maintain the desired temperature over extended periods of time. For example, both monohydroxyl alcohols and glycols, such as methanol and ethylene glycol, are known to react with glutaraldehyde so that even though addition of methanol or ethylene glycol to an aqueous solution of glutaraldehyde initially depresses the freezing point, upon storage, the freezing point rises as the alcohol and glycol react with the glutaraldehyde to form a mixture containing acetal linkages. Therefore, it is desirable to have a stable fixed freezing point.

DESCRIPTION OF THE INVENTION

It has been found that the addition of a catalytic amount of a strong acid to an aqueous solution comprising a dialdehyde and an aliphatic monohydroxyl alcohol and/or polyhydroxyl alcohol freeze point depressant rapidly catalyzes the formation of an equilibrium mixture of the dialdehyde, acetal, and freeze point depressant, which equilibrium mixture has a stable and fixed freezing point.

It has also been found that in order to rapidly and efficiently liberate the dialdehyde for active chemical or biological reactions, dilution of the equilibrium mixture with water and the further addition of a catalytic amount of a strong acid is necessary.

The aliphatic monohydroxyl alcohols which may be used as freeze point depressants herein contain from 1 to 4 carbon atoms, such as methanol, ethanol and the like, and mixtures thereof. The preferred monohydroxyl alcohol is methanol.

The aliphatic polyhydroxyl alcohol which may be employed in this invention as freezing point depressants contain from 2 to 6 carbon atoms, and include ethylene glycol, propylene glycol, glycerol and the like, and mixtures thereof. The preferred polyol is ethylene glycol.

It is understood that one or more aliphatic monohydroxyl alcohols may be mixed with one or more aliphatic polyhydroxyl alcohol.

The acids which are suitable for use in this invention are acids capable of achieving an aqueous pH below about 3.0, preferably below about 2.0, and include phosphoric acid, hydrochloric acid, sulfuric acid, trifluoromethylsulfonic acid, para-toluenesulfonic acid, as well as supported acid catalysts, such as Amberlyst which is a supported arylsulfonic acid (sold by Rohm & Haas Company) and Nafion which is a supported fluorosulfonic acid (sold by E. I. duPont de Nemours Co.).

In order to achieve a stable freeze point depressed product, the aqueous solution generally contains from about 0.1 to about 50 percent by weight of the dialdehyde; from about 5 to about 40 percent by weight of the monohydroxyl alcohol and/or polyhydroxyl alcohol and a catalytic amount of a strong acid, with the remainder of the solution being water such that the total solution is 100 percent by weight. A preferred solution contains 25 percent by weight of dialdehyde, 30 percent by weight of monohydroxyl alcohol and/or polyhydroxyl alcohol and 45 percent by weight of water.

In order to rapidly and efficiently liberate the dialdehyde for active chemical or biological reactions, the aqueous solution should contain from about 0.01 to about 10 percent of the dialdehyde and a catalytic amount of an acid, and may contain up to about 40 percent by weight of the monohydroxyl alcohol and/or polyhydroxyl alcohol, with the remainder of the solution being water such that the total solution is 100 percent by weight.

The solutions may contain other additives such as colorants, surfactants, chelating agents, pH buffers, and the like.

EXAMPLES

The following examples serve to give specific illustrations of the practice of this invention but they are not intended in any way to limit the scope of this invention.

CONTROL A

The freezing point of a mixture of 25 percent by weight of glutaraldehyde and 75 percent by weight of water is 22° F. (as determined by the procedure as set forth in ASTM D-1177-65).

CONTROL B

The following ingredients were mixed:
25 percent by weight of glutaraldehyde,
25 percent by weight of methanol, and
50 percent by weight of water.

The freezing point of the mixture was −20.5° F. and the pH was about 4.0. After storage for 55 days at about 25° C., the freezing point of the mixture was measured and found to be −9.5° F.

CONTROL C

The following ingredients were mixed:
25 percent by weight of glutaraldehyde,
25 percent by weight of ethylene glycol, and
50 percent by weight of water.

The freezing point of the mixture was −14.0° F. and the pH was about 4.0. After storage for 55 days at about 25° C., the freezing point of the mixture was measured and found to be −7.5° F.

EXAMPLE 1

The following ingredients were mixed:
25 percent by weight of glutaraldehyde,
25 percent by weight of methanol, and
50 percent by weight of water.

A one percent solution of phosphoric acid was added to the solution until a pH of 1 to 2 was achieved.

The freezing point of the equilibrium mixture was −9.0° F.

EXAMPLE 2

The following ingredients were mixed:
25 percent by weight of glutaraldehyde,
25 percent by weight of ethylene glycol, and
50 percent by weight of water.

A one percent solution of phosphoric acid was added to the solution until a pH of 1 to 2 was achieved.

The freezing point of the mixture was 3° F.

The aqueous equilibrium mixtures in Examples 1 and 2 were formed in less than about 3 hours. These equilibrium mixtures are able to maintain the stated freezing point over long periods of time, even after 6 months of storage.

In contradistinction, the freezing points of the mixtures of Controls A and B varied significantly after only 55 days and up to three months may be required for the solution to achieve equilibrium.

EXAMPLES 3 TO 7

In these examples, the following ingredients were mixed:
25 percent by weight of glutaraldehyde,
30 percent by weight of methanol, and
45 percent by weight of water.

This mixture was stored for about 6 months. The final equilibrium of the mixture had been reached at this point in time. This mixture was diluted to 0.1% of theoretical glutaraldehyde. To separate portions of the mixture was added a one percent solution of phosphoric acid until the desired pH was achieved. The percent of glutaraldehyde recovered from the mixture at various times and pH values is shown in Table I. The glutaraldehyde levels were determined by gas chromatography.

TABLE I

| Example | Time (hrs) | pH 2 | 3 | 4 | 5 | 10 |
|---|---|---|---|---|---|---|
| 3 | 1.0 | 90% | 77% | 58% | — | — |
| 4 | 3.0 | 93% | 78% | — | — | — |
| 5 | 5.0 | 93% | 81% | 58% | — | — |
| 6 | 24.0 | 97% | 93% | 69% | 37% | 44% |
| 7 | 48.0 | 94% | 93% | 73% | 37% | 44% |

EXAMPLES 8 TO 13

In these Examples, the following ingredients were mixed:
25 percent by weight of glutaraldehyde,
30 percent by weight of ethylene glycol, and
45 percent by weight of water.

This mixture was stored for 6 months. The final equilibrium of the mixture had been reached. This mixture was diluted to 0.1% of theoretical glutaraldehyde. To separate portions of the mixture was added a one percent solution of phosphoric acid until the desired pH was achieved. The percent of glutaraldehyde recovered from the mixture at various times and pH values is shown in Table II. The glutaraldehyde levels were determined by gas chromatography.

TABLE II

| Example | Time (hrs) | pH 2 | 3 | 4 | 5 | 10 |
|---|---|---|---|---|---|---|
| 8 | 1.0 | — | — | 50% | — | — |
| 9 | 1.67 | 77% | 54% | — | — | — |
| 10 | 2.17 | 81% | 66% | — | — | — |
| 11 | 3.0 | — | — | — | 59% | 57% |
| 12 | 24.0 | 99% | 76% | 54% | — | — |
| 13 | 72.0 | — | — | — | 61% | 52% |

What is claimed is:

1. A process for rapidly obtaining a stabilized, depressed freeze point for an aqueous solution comprising (1) water, (2) a dialdehyde and (3) an aliphatic monohydroxyl alcohol containing from 1 to 4 carbon atoms and/or polyhydroxyl alcohol containing from 2 to 6 carbon atoms, which comprises adding a catalytic amount of a strong acid to said solution.

2. A process as defined in claim 1 wherein the dialdehyde is glutaraldehyde.

3. A process as defined in claim 1 wherein the aliphatic monohydroxyl alcohol is methanol.

4. A process as defined in claim 1 wherein the aliphatic polyhydroxyl alcohol is ethylene glycol.

5. A process for liberating a dialdehyde from an aqueous equilibrium mixture, having a stabilized, depressed freeze point, comprising (1) water, (2) a dialdehyde, (3) acetal, (4) an aliphatic monohydroxyl alcohol containing from 1 to 4 carbon atoms and/or polyhydroxyl alcohol containing from 2 to 6 carbon atoms and (5) aqueous residue of a strong acid by first diluting the mixture with water and then adding a catalytic amount of a strong acid.

6. A process as defined in claim 5 wherein the dialdehyde is glutaraldehyde.

7. A process as defined in claim 5 wherein the aliphatic monohydroxyl alcohol is methanol.

8. A process as defined in claim 5 wherein the aliphatic polyhydroxyl alcohol is ethylene glycol.

9. A process for rapidly obtaining a stabilized, depressed freeze point for an aqueous solution comprising from about 0.1 to about 50 percent by weight of a dialdehyde, from about 5 to about 40 percent by weight of an aliphatic monohydroxyl alcohol containing from 1 to 4 carbon atoms and/or polyhydroxyl alcohol containing from 2 to 6 carbon atoms and the remainder water which comprises adding a catalytic amount of a strong acid to said solution.

10. A process for liberating a dialdehyde from an aqueous equilibrium mixture comprising (1) water, (2) from about 0.01 to about 10 percent by weight of a dialdehyde, (3) acetal, (4) an aliphatic monohydroxyl alcohol containing from 1 to 4 carbon atoms and/or polyhydroxyl alcohol containing from 2 to 6 carbon atoms, and (5) aqueous residue of a strong acid, which comprises first diluting the mixture with water and then adding a catalytic amount of a strong acid.

11. A process for rapidly obtaining a stabilized, depressed freeze point for an aqueous solution comprising (1) water, (2) a dialdehyde and (3) an aliphatic monohydroxyl alcohol containing from 1 to 4 carbon atoms and/or polyhydroxyl alcohol containing from 2 to 6 carbon atoms, which comprises adding a catalytic amount of a strong acid to said solution, to produce an equilibrium mixture of water, the dialdehyde, acetal, strong acid residue and the aliphatic monohydroxyl alcohol and/or polyhydroxyl alcohol, then diluting the mixture with water and adding a catalytic amount of a strong acid to liberate the dialdehyde.

* * * * *